United States Patent
Li et al.

(10) Patent No.: US 7,662,364 B2
(45) Date of Patent: Feb. 16, 2010

(54) DRUG FOR HYPERPHOSPHEREMIA AND ITS PREPARATIVE METHOD

(76) Inventors: Shi Biao Li, No. 81 East Qianfoshan Road, Jinan (CN) 250013; Min Qiao, No. 81 East Qianfoshan Road, Jinan (CN) 250013; Wei Sheng Zhang, No. 81 East Qianfoshan Road, Jinan (CN) 250013

( * ) Notice: Subject to any disclaimer, the term of this patent is extended or adjusted under 35 U.S.C. 154(b) by 370 days.

(21) Appl. No.: 11/576,731

(22) PCT Filed: Jun. 26, 2006

(86) PCT No.: PCT/CN2006/001463

§ 371 (c)(1),
(2), (4) Date: Apr. 5, 2007

(87) PCT Pub. No.: WO2007/109929

PCT Pub. Date: Oct. 4, 2007

(65) Prior Publication Data

US 2009/0016984 A1     Jan. 15, 2009

(30) Foreign Application Priority Data

Mar. 24, 2006   (CN) .................. 2006 1 0043267

(51) Int. Cl.
*A61K 31/74* (2006.01)
*A61K 31/7135* (2006.01)
(52) U.S. Cl. ................. 424/78.1; 424/78.34; 424/78.31
(58) Field of Classification Search ........................ None
See application file for complete search history.

(56) References Cited

U.S. PATENT DOCUMENTS

| 5,968,976 | A  | * | 10/1999 | Murrer et al. ............... 514/492 |
| 6,703,013 | B1 | * | 3/2004 | Ninomiya et al. .......... 424/78.1 |
| 2006/0047086 | A1 | * | 3/2006 | Albright .................... 525/340 |

* cited by examiner

*Primary Examiner*—Robert A Wax
*Assistant Examiner*—William Craigo
(74) *Attorney, Agent, or Firm*—Global IP Services; Tianhua Gu

(57) ABSTRACT

This invention reports a drug for hyperpheremia and its preparative method. The preparation includes active constituents, lanthanum polystyrene sulfonate, and excipients. The preparative method in the invention can be summarized as follows: Polystyrene sulfonic acid is obtained by treating polystyrene sulfosalt with hydrochloric acid, soaked or eluted with water soluble lanthanum-contained solution, and washed with water till its PH is neutral. Then, the lanthanum polystyrene sulfonate solution is washed till the superfluous $La^-$ unexchanged is washed out. Lanthanum polystyrene sulfonate is taken out and crushed to powder after being dried. The lanthanum polystyrene sulfonate, whose weight percentage of lanthanum is 14-22%, is used as active constituents to prepare gastrointestinal tract preparations together with general amount of excipients with routine preparative method. In the invention, lanthanum polystyrene sulfonate is adopted as active constituents, mixed with excipients, and the preparation is obtained. It makes phosphate in alimentary tract become insoluble conjugates after gastrointestinal tract administration. The insoluble conjugates would be discharged. Thus, the drug can achieve the purpose of treating hyperpheremia.

5 Claims, No Drawings

DRUG FOR HYPERPHOSPHEREMIA AND ITS PREPARATIVE METHOD

FIELD OF THE INVENTION

The invention involves in a drug, especially a drug for hyperphospheremia and its preparative method.

BACKGROUND OF THE INVENTION

Hyperphospheremia is one of the complications following renal failure, hypoparathyroid and some other diseases, with the result of serious disorders in calcium and phosphonium metabolism. At present, the treatment for hyperphospheremia includes dialysis and oral administration of aluminium compounds, calcium compounds and lanthanum carbonate aquated complex etc. They all have some disadvantages. Dialysis would cause serious damage to body and would not decrease phosphate concentration significantly. With great systematic adverse reactions, oral aluminium and calcium compounds could damage kidney, skin, internal organs, brain and bone. Thus, they are applied clinically with limited doses. Oral lanthanum carbonate aquated complex just dissolves in solutions to remove ingested phosphate, whose PH is similar to that of gastric juice. But, it does not dissolve in solutions, whose PH is similar to that of intestinal juice. Therefore, oral lanthanum carbonate aquated complex would not remove phosphate in intestinal juice significantly. In addition, American patent reported one kind of amine polymer, with capability of removing phosphate radical in vivo. It is able to decrease phosphate in gastrointestinal tract, however, its synthesis costs are high and the produce costs would increase accordingly. Thus, it would add heavily economic burden to patients. Technologists in this field have been seeking a drug, which could play its role in different PH of the whole gastrointestinal tract. They tried to decrease its costs, with the final aim to further relieve the economic burden of patients.

CONTENT OF THE INVENTION

The purpose of this invention is to provide a drug for hyperphospheremia and its preparative method. The preparation includes lanthanum active constituents of the invention drug, polystyrene sulfonate, and excipients. It makes phosphate in alimentary tract become insoluble conjugates after gastrointestinal tract administration. The insoluble conjugates would be discharged. Thus, the drug can achieve the purpose of treating hyperphospheremia.

The formula is proposed in order to achieve the purpose above: a drug for hyperphospheremia is made up of lanthanum polystyrene sulfonate as active constituents and excipients. The general formula of lanthanum polystyrene sulfonate is as follows:

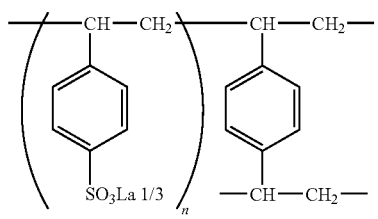

The weight percentage of lanthanum in lanthanum polystyrene sulfonate is 14-22%.

The weight percentage of lanthanum in lanthanum polystyrene sulfonate is 16-22%.

One drug for hyperphospheremia: Its lanthanum polystyrene sulfonate is used for the treatment of hyperphospheremia through gastrointestinal tract administration.

The dosage form is pulveres, capsules, tablets, dry suspensions, suspensions or drug granules.

The preparative method of a drug for hyperphospheremia can be characterized by the following: Polystyrene sulfonic acid is obtained by treating polystyrene Sulfosalt with hydrochloric acid, soaked or eluted with water soluble lanthanum-contained solution, and washed with water till its PH is neutral. Then, the lanthanum polystyrene sulfonate solution is washed till the superfluous La⁻ unexchanged is washed out. Lanthanum polystyrene sulfonate is taken out and crushed to powder after being dried. The lanthanum polystyrene sulfonate, whose weight percentage of lanthanum is 14-22%, is used as active constituents to prepare gastrointestinal tract preparations together with general amount of excipients with routine preparative method. Polystyrene sulfonic acid is soaked or eluted with water soluble lanthanum-contained solution at 0° C.-60° C., 5-30 h. The weight percentage of lanthanum in lanthanum polystyrene sulfonate obtained as stated preparative method is 14-22%. The dosage form obtained from lanthanum polystyrene sulfonate and excipients is pulveres, capsules, drug granules, dry suspensions, suspensions or tablets. The water soluble lanthanum-contained solution in the preparative method is lanthanum nitrate, lanthanum chloride, lanthanum sulfate or lanthanum acetate.

The researchers of this invention have found in practice that lanthanum polystyrene sulfonate possess great efficacy of removing phosphate in the whole alimentary tract of human, including stomach, small intestine and large intestine. Lanthanum of lanthanum polystyrene sulfonate would reduce its release into alimentary juice with less phosphate in alimentary juice; otherwise, it would increase its release with more phosphate in alimentary juice. Thus, they decide that Lanthanum polystyrene sulfonate has great clinical significance.

Further researches have indicated that lanthanum polystyrene sulfonate has relatively significant effect in removing phosphate of human stomach, small intestine and large intestine. Experiments are as follows:

Basic solution 1: Na2HPO4 14 g and NaCl 8.5 g were dissolved in distilled water 1000 ml, whose PH was adjusted to 3 with hydrochloric acid. Phosphate content was determined after the solution was filtered.

Basic solution 2: Na2HPO4 14 g and NaCl 8.5 g were dissolved in distilled water 1000 ml, whose PH was adjusted to 6.8 with hydrochloric acid. Phosphate content was determined after the solution was filtered.

Basic solution 3: Na2HPO4 14 g and NaCl 8.5 g were dissolved in distilled water 1000 ml, whose PH was adjusted to 7.8 with hydrochloric acid. Phosphate content was determined after the solution was filtered.

Lanthanum polystyrene sulfonate of different quantities was added to Basic solution 1, 2 and 3, respectively. The ratio of lanthanum and phosphate was adjusted to 3:1 and the mixture was stirred at 37° C. Certain solution was taken out at some intervals to determine phosphate content and compute the percentage of removing phosphate. The results were shown as in the table.

| Time (min) | Removing phosphate % | | |
|---|---|---|---|
| | Basic solution 1 | Basic solution 2 | Basic solution 3 |
| 10 | 94.5 | 97.2 | 96.4 |
| 20 | 95.2 | 98.0 | 96.6 |
| 30 | 95.7 | 98.3 | 96.8 |
| 60 | >96.0 | >98.0 | >98.0 |

The results in the table above showed that lanthanum polystyrene sulfonate had almost identical effectiveness in different solutions, whose PH were respectively similar to that of human stomach, small intestine and large intestine.

In order to further prove the safety of the drug, experiments were carried out to show that lanthanum of lanthanum polystyrene sulfonate would reduce its release with less phosphate in alimentary juice. Experiments were as follows:

Phosphate of different quantities was added to lanthanum polystyrene sulfonate respectively. The ratio of lanthanum and phosphate was adjusted to 1:0.2, 1:0.1, 1:0.05 and 1:0. They were added to 0.85% NaCl (pH6.8) solution, stirred for 10 minutes at 37° C. Then, lanthanum content of different solutions was determined and lanthanum content unreleased in lanthanum polystyrene sulfonate was worked out. The results were 19%, 43%, 68% and 91% respectively, which indicated that lanthanum would reduce its release with less phosphate in solutions.

To prove the drug of this invention makes difference in removing phosphate, compared with lanthanum carbonate, experiments were carried out to determine the effectiveness of lanthanum carbonate removing phosphate in different solutions, whose PH were respectively similar to that of human small intestine and large intestine.

Lanthanum carbonate 0.5 g was added to 0.85% NaCl solution 100 ml (pH 6.8) and 0.85% NaCl solution 100 ml (pH7.8), respectively. Then, sufficient quantities of $Na_2HPO_4$ were added to the two solutions, stirred for 37° C. Filtered solutions were obtained at 10 min, 30 min, 40 min and 60 min, respectively. Phosphate content was determined and the percentage of removing phosphate was computed. Results were shown as in the table.

| Time (min) | Removing phosphate % 0.85% NaCl pH 6.8 | Removing phosphate % 0.85% NaCl pH 7.8 |
|---|---|---|
| 10 | 6.7 | 1.4 |
| 30 | 13.7 | <2.0 |
| 40 | 16.9 | <2.0 |
| 60 | 20.8 | <2.0 |

The results indicated that lanthanum carbonate removed less phosphate in the solution whose PH was similar to that of human small intestine and it was unable to remove phosphate in the solution whose PH was similar to that of human large intestine.

The amount of lanthanum in lanthanum polystyrene sulfonate obtained with the preparative method stated in the invention was concerned with the reaction temperature and time between polystyrene sulfosalt and water soluble lanthanum-contained solution, on condition that the amount of water soluble lanthanum-contained solution was determined. The longer the time was, the more lanthanum was obtained; Otherwise, the less lanthanum was obtained. The higher the temperature was, the more lanthanum was obtained; Otherwise, the less lanthanum was obtained. Experiment data in the table were further proved.

The weight ratio of polystyrene sulfosalt and lanthanum nitrate was 1:2 in the sample 1, 2, 3 and 4. The lanthanum polystyrene sulfonate was obtained at different conditions with the preparative method stated in the invention.

| Sample | Temperature (° C.) | Time (hour)/ every time | Weight percentage of lanthanum in lanthanum polystyrene sulfonate (%) |
|---|---|---|---|
| 1 | 50 | 12 | 20 |
| 2 | 50 | 8 | 18 |
| 3 | 30 | 8 | 16 |
| 4 | 20 | 16 | 20 |

The weight ratio of polystyrene sulfosalt and lanthanum chloride was 1:2 in the sample 1, 2, 3 and 4. The lanthanum polystyrene sulfonate was obtained at different conditions with the preparative method stated in the invention.

| Sample | Temperature (° C.) | Time(hour)/ every time | Weight percentage of lanthanum in lanthanum polystyrene sulfonate (%) |
|---|---|---|---|
| 1 | 50 | 16 | 22 |
| 2 | 50 | 8 | 20 |
| 3 | 30 | 12 | 18 |
| 4 | 20 | 8 | 17 |

The temperature in the table above could alter from 0° C. to 60° C. But, when it became lower, the reaction time would be longer accordingly. 30-50° C. is generally adopted in industrialized production.

Pharmacodynamic experiment was follows:

Experiment was conducted to indicate that lanthanum polystyrene sulfonate was effective for treating hyperphosphatemia in chronic renal failure (CRF).

Reagents: lanthanum polystyrene sulfonate; Experimental animals: Wistar male rats, body weight 180-220 g, the total number is 30. The rats were randomly divided into three groups: control, model control and treatment group. ① 10 rats continued to be fed with animal feeds in the control group. Two weeks later, they were given tap water 2 ml/200 g through intragastric administration every day. ② 10 rats were given 0.2% adenine 2 ml/200 g through intragastric administration in the model control group. ③ In the treatment group, 10 rats were given lanthanum polystyrene sulfonate 200 mg/kg through intragastric administration every day, after they were given adenine in the same way for 2 weeks. All the animals should be given intragastric administration for 6 consecutive weeks. In the sixth week, blood was obtained from rats and blood phosphonium concentration was determined. Results were shown as in the table.

| Group | Number | P at the third week (mmol/L) | P in the sixth week (mmol/L) |
|---|---|---|---|
| Control group | 10 | 2.84 ± 0.21 | 2.97 ± 0.28 |
| Model group | 10 | 4.10 ± 0.27 | 4.58 ± 0.34 |
| Treatment group | 10 | 3.22 ± 0.31 | 3.14 ± 0.2 |

The difference in blood phosphonium concentration between model and control group is significant at both the third and the sixth week (P<0.05). The difference in blood phosphonium concentration between treatment and model group is significant at both the third and the sixth week (P<0.05).

Conclusion: Lanthanum polystyrene sulfonate could reduce the blood phosphonium concentration of hyperphosphatemia rats.

The results of all experiments above indicated that lanthanum polystyrene sulfonate had great efficacy of removing phosphate in the stomach, small intestine and large intestine. It made phosphate in the alimentary tract become insoluble conjugates, which would be discharged. Thus, the drug could achieve the purpose of treating hyperphospheremia. Furthermore, the lanthanum of Lanthanum polystyrene sulfonate would reduce its release with less phosphate in the alimentary tract. Polystyrene sulfonic acid was disintegrated from lanthanum polystyrene sulfonate as la$^-$ released, which had little side effect for it was not absorbed by human body. Chinese patent paper 96193918.4 had reported one experiment in which phosphate could be combined without any lanthanum entering into blood. The experiment further provided the safety proof that lanthanum polystyrene sulfonate had no toxicity to body.

The cost of pulveres, drug granules, capsules, dry suspensions, suspensions or tablets made up of lanthanum polystyrene sulfonate and excipients with the preparative method stated in the invention was relatively lower. It was lower than that of amine polymers, though they had the same effect of removing patients' phosphate. Thus, lanthanum polystyrene sulfonate was more suitable to patients of lower incomes and it would reduce the economic burden of patients who had to use the drug for long time. It ensured that more patients could use low side effect drugs, which could sufficiently remove phosphate in the gastrointestinal tract.

The preparation of one drug for hyperphospheremia in the invention is made up of lanthanum polystyrene sulfonate as active constituents and excipients, which are gastrointestinal tract administered.

Lanthanum polystyrene sulfonate' general formula is as follows:

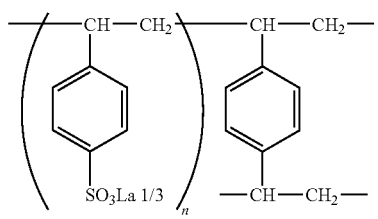

The weight percentage of lanthanum in lanthanum polystyrene sulfonate is 14-22%, which may be less than 14%. The administration dosage should be increased accordingly, when lanthanum weight percentage is less than 14%. The further preferred weight percentage of lanthanum in lanthanum polystyrene sulfonate is 16-22%. The preparation in this invention may be pulveres, drug granules, capsules, dry suspensions, suspensions or tablets. Any weight percentage of 16%, 17%, 18%, 19%, 20%, 21% or 22% of lanthanum in lanthanum polystyrene sulfonate power is added by aspartame as general amount of excipients, and pulveres are obtained, which could be used as enema; Added by hydroxy-propyl methyl cellulose as general amount of excipients, mixed even, and dry suspensions are obtained; Added by hydroxy-propyl methyl cellulose and warter as general amount of excipients, mixed evenly, and dry suspensions are obtained; Added by capsules or tablets excipients of general amount, and capsules or tablets are obtained. The excipients stated in the invention could use any one popular in the medicine field, not limited to this example.

The drug containing lanthanum polystyrene sulfonate stated in the invention would treat any symptoms due to hyperphospheremia, through gastrointestinal tract administration. The results of our experiments indicated that lanthanum polystyrene sulfonate would be prepared as any dosage form of gastrointestinal tract administration, with the ability of treating hyperphospheremia. The oral amount per day for adults of the invention drug is 3-10 g, which is referred to lanthanum polystyrene sulfonate weight. The oral amount for children or special patients will be altered at different conditions, or administered as the physician suggests.

The preparative method of a drug for hyperphospheremia can be characterized by the following: Polystyrene sulfonic acid is obtained by treating polystyrene Sulfosalt with hydrochloric acid, soaked or eluted with water soluble lanthanum-contained solution, and washed with water till its PH is neutral. Then, the lanthanum polystyrene sulfonate solution is washed till the superfluous La$^-$ unexchanged is washed out. Lanthanum polystyrene sulfonate is taken out and crushed to powder after being dried. The lanthanum polystyrene sulfonate, whose weight percentage of lanthanum, is 14-22% is used as active constituents to prepare preparations together with general amount of excipients with routine preparative method. Polystyrene sulfosalt would be sodium polystyreme sulphonate, calcium polystyreme sulphonate, potassium polystyreme sulphonate and magnesium polystyreme sulphonate etc. But, sodium polystyreme sulphonate and calcium polystyreme sulphonate are adopted mainly, when the production costs are considered to be reduced. Water soluble lanthanum-contained solution would be lanthanum nitrate, lanthanum chloratum, lanthanum slfuricum and lanthanum acetate. Polystyrene sulfonic acid is obtained by treating polystyrene sulfosalt with hydrochloric acid, and soaked or eluted with water soluble lanthanum-contained solution at 0° C.-60° C. (20° C.-50° C. preferred), for 4-35 h (8-20 h preferred). Of course, standing or eluting time is still concerned with the concentration of water soluble lanthanum-contained solution and thus it could be adjusted in accordance with the concentration in order to achieve complete reactions. To further refine drug, polystyrene sulfosalt could be soaked in alcohol to remove some foreign materials, after soaked and washed. Although, this procedure could also be carried out after lanthanum polystyrene sulfonate is obtained, it brought trouble to the production. The concentration of water soluble lanthanum-contained solution could be prepared based on different requirements and thus standing or eluting time adjusted accordingly. The weight percentage of lanthanum in lanthanum polystyrene sulfonate obtained as preparative method above is 14-22% (preferred 16-22%). The water of related preparative method would better be distilled water.

Specific preparative methods are exemplified as below:

1. Sodium polystyreme sulphonate 100 g is dealt with hydrochloric acid and polystyrene sulfonic acid is obtained. Polystyrene sulfonic acid is soaked with 50% lanthanum nitrate 400 ml for 8 h, at 50° C. The solution is washed with water till its PH is almost neutral. Then, the superfluous la$^-$ unexchanged is washed out. Lanthanum polystyrene sulfonate is taken out and crushed to powder after being dried. The weight percentage of lanthanum in lanthanum polystyrene sulfonate obtained is 16%. The preparation is made up of lanthanum polystyrene sulfonate power and general amount of excipients with routine preparative method.

2. Calcium polystyreme sulphonate 100 g is dealt with hydrochloric acid and polystyrene sulfonic acid is obtained. Polystyrene sulfonic acid is soaked with 40% lanthanum nitrate 500 ml for 20 h, at 20° C. The solution is washed with water till its PH is almost neutral. Then, the superfluous la⁻ unexchanged is washed out. Lanthanum polystyrene sulfonate is taken out and crushed to powder after being dried. The weight percentage of lanthanum in lanthanum polystyrene sulfonate obtained is 14%. The preparation is made up of lanthanum polystyrene sulfonate power and general amount of excipients with routine preparative method.

3. Sodium polystyreme sulphonate 100 g is dealt with hydrochloric acid and polystyrene sulfonic acid is obtained. Wet polystyrene sulfonic acid is put into column. The temperature of column body is kept at 60° C. 50% lanthanum nitrate 400 ml is used to elute foreign materials for 4 h, twice or three times. The solution in column is washed with water till its PH is almost neutral. Then, the superfluous la⁻ unexchanged is washed out. Lanthanum polystyrene sulfonate is taken out and crushed to powder after being dried. The weight percentage of lanthanum in lanthanum polystyrene sulfonate obtained is 19%. The preparation is made up of lanthanum polystyrene sulfonate power and general amount of excipients with routine preparative method.

4. Sodium polystyreme sulphonate 100 g is soaked with distilled water and then washed with distilled water till washings are clean. The solution is soaked with alcohol to remove foreign materials and dealt with hydrochloric acid. Polystyrene sulfonic acid is obtained and soaked with 50% lanthanum nitrate 400 ml for 8 h, at 30° C. The solution is washed with distilled water till its PH is almost neutral. Then, the superfluous la⁻ unexchanged is washed out. Lanthanum polystyrene sulfonate is taken out and crushed to powder after being dried. The weight percentage of lanthanum in lanthanum polystyrene sulfonate obtained is 16%. When 1% aspartame is added and mixed, powders are obtained; When thin syrup is added as adhesive materials, drug granules are obtained; When 2.5% hydroxy-propyl methyl cellulose is added and blended, dry suspensions are obtained; When some water is added to dry suspensions, suspensions are obtained; Capsule and tablet are made up of lanthanum polystyrene sulfonate and general amount of excipients with routine preparative method.

5. Sodium polystyreme sulphonate 100 g is soaked with distilled water and then washed with distilled water till washings are clean. The solution is soaked with alcohol to remove foreign materials and dealt with hydrochloric acid. Then, polystyrene sulfonic acid is obtained. Wet polystyrene sulfonic acid is put into column, the temperature of which is kept at 50° C. 50% lanthanum chloratum 400 ml is used to elute foreign materials once, twice or three times. Every elution time would be 16 h. The solution in column is washed with water till its PH is almost neutral. Then, the superfluous la⁻ unexchanged is washed out. Lanthanum polystyrene sulfonate is taken out, dried and crushed. The weight percentage of lanthanum in lanthanum polystyrene sulfonate obtained is 22%, which is added by 5% starch paste, dried, and tablet is obtained.

6. Calcium polystyreme sulphonate 100 g is soaked with distilled water and then washed with distilled water till washings are clean. The solution is soaked with alcohol to remove foreign materials and dealt with hydrochloric acid. Polystyrene sulfonic acid is obtained and soaked with 40% lanthanum slfuricum 500 ml for 8 h, at 20° C. The solution is washed with distilled water till its PH is almost neutral. Then, the superfluous la⁻ unexchanged is washed out. Lanthanum polystyrene sulfonate is dried and crushed below 80° C., after being taken out. The weight percentage of lanthanum in lanthanum polystyrene sulfonate obtained is 14%. The preparation is made up of lanthanum polystyrene sulfonate power and general amount of excipients with routine preparative method.

7. Magnesium polystyreme sulphonate 100 g is soaked with distilled water and then washed with distilled water till washings are clean. The solution is soaked with alcohol at least 8 h in order to remove foreign materials and dealt with hydrochloric acid. Polystyrene sulfonic acid is obtained and soaked with 30% lanthanum slfuricum 600 ml for three times. The temperature of solution is kept at 35° C. and steted for 8 h. In the first two times, the solution is washed with distilled water till its PH is almost neutral. In the last time, the superfluous la⁻ unexchanged is washed out with distilled warter. Lanthanum polystyrene sulfonate is taken out, dried and crushed to powder. The weight percentage of lanthanum in lanthanum polystyrene sulfonate obtained is 18%. The preparation is made up of lanthanum polystyrene sulfonate power and general amount of excipients with routine preparative method.

8. Potassium polystyreme sulphonate 100 g is soaked with distilled water and then washed with distilled water till washings are clean. The solution is soaked with alcohol at least 8 h in order to remove foreign materials and dealt with hydrochloric acid. Polystyrene sulfonic acid is obtained and soaked with 50% lanthanum slfuricum 400 ml for twice. The temperature of solution is kept at 20° C. and steted for 16 h. The solution is washed with distilled water till its PH is almost neutral in the first time. The superfluous la⁻ unexchanged is washed out with distilled warter in the latter time. Lanthanum polystyrene sulfonate is taken out, dried and crushed to powder. The weight percentage of lanthanum in lanthanum polystyrene sulfonate obtained is 20%. The preparation is made up of lanthanum polystyrene sulfonate power and general amount of excipients with routine preparative method.

The weight percentage of lanthanum in lanthanum polystyrene sulfonate in this invention is 14-22%, as the weight of lanthanum polystyrene sulfonate is 100.

What is claimed is:

1. A pharmaceutical composition for hyperphospheremia comprising an active ingredient of lanthanum polystyrene sulfonate and excipients, the general formula of the lanthanum polystyrene sulfonate resin being:

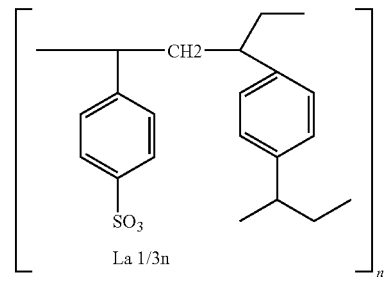

Wherein "n" is an integer;
 the amount of lanthanum in said lanthanum polystyrene sulfonate resin being 14-22 wt %;
 said lanthanum polystyrene sulfonate is an active ingredient of a pharmaceutical composition for the treatment of hyperphospheremia through gastrointestinal tract administration;
 said lanthanum polystyrene sulfonate is administered as a pharmaceutical dosage form selected from the group consisting of a powder, capsules, tablets, dried suspensions, suspensions and granular formulations.

2. The pharmaceutical composition of claim 1 wherein the amount of lanthanum in said lanthanum polystyrene sulfonate is 16-22 wt %.

3. A method for preparing the pharmaceutical composition of claim 1 comprising:
 obtaining polystyrene sulfonic acid by acidifying polystyrene sulfosalt with hydrochloric acid;
 loading the resin by soaking or washing the polystyrene sulfonic acid with a lanthanum solution;
 washing with water to remove free protons and lanthanum ions;
 drying and crushing the resin to a powder to obtain a lanthanum polystyrene sulfonate resin with a lanthanum content of 14-22 wt %;
 combining the obtained resin with pharmaceutically acceptable excipients by routine methods.

4. The method of claim 3, wherein the loading step is done between 0-60 degrees Celsius, and the washing step is done for 5-30 hours.

5. The method of claim 3 wherein the lanthanum solution is selected from the group consisting of lanthanum nitrate, lanthanum chloride, lanthanum sulfate and lanthanum acetate.

* * * * *